(12) United States Patent
Standke et al.

(10) Patent No.: US 9,200,014 B2
(45) Date of Patent: Dec. 1, 2015

(54) DECHLORINATION OF ALKYL-FUNCTIONAL ORGANOSILANES AND ALKYL-FUNCTIONAL ORGANOSILOXANES

(75) Inventors: Burkhard Standke, Loerrach (DE); Mustafa Guezelsahin, Loerrach (DE); Manuel Friedel, Zurich (CH); Joerg Arndt, Grenzach-Wyhlen (DE); Klaus Koellisch, Rheinfelden (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/007,137

(22) PCT Filed: Feb. 27, 2012

(86) PCT No.: PCT/EP2012/053244
§ 371 (c)(1),
(2), (4) Date: Oct. 14, 2013

(87) PCT Pub. No.: WO2012/126699
PCT Pub. Date: Sep. 27, 2012

(65) Prior Publication Data
US 2014/0024849 A1    Jan. 23, 2014

(30) Foreign Application Priority Data
Mar. 24, 2011   (DE) .......................... 10 2011 006 053

(51) Int. Cl.
*C07F 7/20* (2006.01)
*C07F 7/18* (2006.01)
*B01J 41/04* (2006.01)
*B01J 41/12* (2006.01)
*B01J 47/00* (2006.01)
*B01D 15/36* (2006.01)

(52) U.S. Cl.
CPC ................. *C07F 7/18* (2013.01); *B01J 41/046* (2013.01); *B01J 41/125* (2013.01); *B01J 47/006* (2013.01); *C07F 7/188* (2013.01); *C07F 7/1868* (2013.01); *C07F 7/20* (2013.01); *B01D 15/363* (2013.01)

(58) Field of Classification Search
USPC .......................................... 556/466, 467, 482
See application file for complete search history.

(56) References Cited

U.S. PATENT DOCUMENTS 4,924,022 A * 5/1990 Bank et al. .................... 556/471
6,727,375 B2   4/2004 Steding et al.

FOREIGN PATENT DOCUMENTS

EP   0 421 644   4/1991
EP   0 672 640   9/1995

OTHER PUBLICATIONS

Sigma-Aldrich; www.sigmaaldrich.com/catalog/product/aldrich/216410?lang=en&region=US, downloaded on Oct. 27, 2014.*
Rohm and Hass; pp. 1-2, Oct. 8, 2008.*
Dow, Dowex MWA-1 resin literature; Apr. 2002.*
International Search Report Issued Apr. 19, 2012 in PCT/EP12/53244 Filed Feb. 27, 2012.

* cited by examiner

*Primary Examiner* — Sudhakar Katakam
*Assistant Examiner* — Pancham Bakshi
(74) *Attorney, Agent, or Firm* — Oblon, McClelland, Maier & Neustadt, L.L.P.

(57) ABSTRACT

The invention relates to a process for dechlorinating alkylsilanes and siloxanes, and also to the use of basic anion exchanger resins for dechlorinating alkyl silanes and alkylsiloxanes.

15 Claims, 1 Drawing Sheet

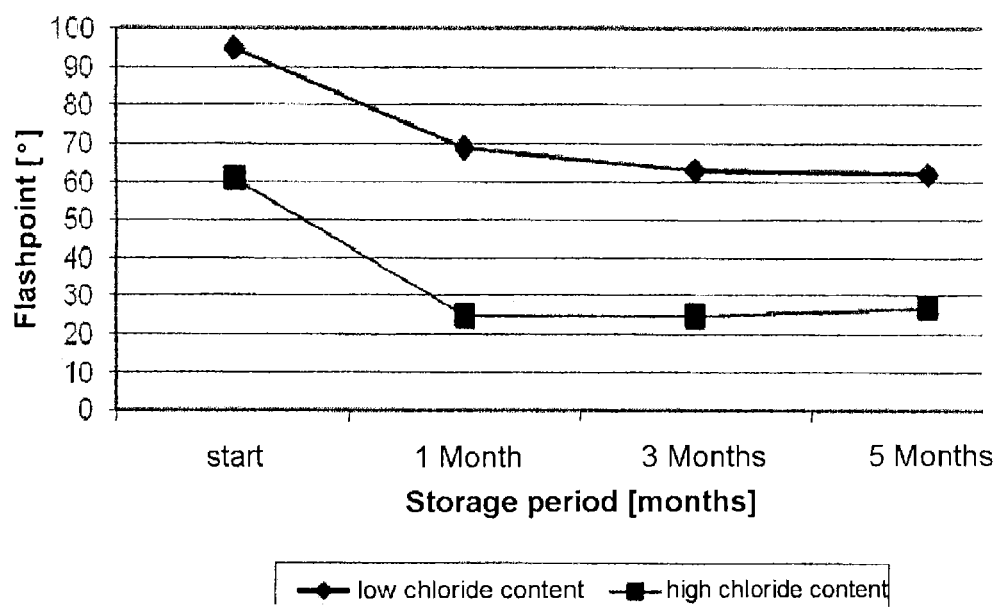

DECHLORINATION OF ALKYL-FUNCTIONAL ORGANOSILANES AND ALKYL-FUNCTIONAL ORGANOSILOXANES

The invention relates to a process for dechlorinating alkylsilanes and siloxanes, hereinafter referred to as alkyl-functional organosilanes, and also to the use of basic anion exchanger resins for dechlorinating alkyl-functional organosilanes, such as alkylsilanes and siloxanes.

EP 0 741 137 B1 discloses reducing the level of organo-functionally bound unconverted chlorine in the production of amino-functional organosilanes by reacting the said organosilanes, substituted with unhydrolyzable chlorides, with a metal alkoxide in a downstream distillative work-up. Sodium ethoxide is used for example. EP 0 702 017 B1 relates to a two-step reaction to reduce organo-functionally bound chlorides in silanes with metal oxides dissolved in alcohols. The processes mentioned are very involved analytically and therefore more useful for reacting unhydrolyzable chlorides.

EP 0 999 214 B1 discloses a process for preparing alkoxysilanes low in or essentially free of acidic chloride by treating the reaction product of a chlorosilane with an alcohol in water- and solvent-free phase, from which hydrogen chloride was removed, with liquid or gaseous ammonia at 10 to 50° C. Salts formed are removed and the product is distilled. The level of hydrolyzable chloride can be reduced to about 10 ppm using this process. A further reduction in the hydrolyzable chloride content requires an additional treatment with a sodium methoxide solution for example.

This treatment is inconvenient, since it is first necessary to determine the level of hydrolyzable chloride as well as the amounts of ammonia and sodium methoxide solution to be added. The treatment with alkali metal alkoxides to reduce the residual chloride content, what is more, is disadvantageous because it may result in the case of alkyl-functional siloxanes in an undesired additional condensation with undesired molecular weight increase and viscosity elevation.

It is long known to prepare alkyltrialkoxysilanes and alkylalkoxysiloxanes from the corresponding chlorosilane compounds. However, using chlorosilanes, especially alkylchlorosilanes, means that the products do contain certain residual amounts of chlorides. The chlorides can be present in the products in bound form, for example as alkyldialkoxychlorosilane and alkylalkoxychlorosiloxane, respectively, or in free form as hydrogen chloride (HCl) for example. Free HCl and also hydrolyzable chlorides attached to silicon atoms (Si—Cl) can be quantified together via a potentiometric titration.

The chlorides thus quantifiable are hereinbelow referred to as hydrolyzable chlorides.

The products formed in customary processes for producing alkyltrialkoxysilanes and/or alkylalkoxysiloxanes, hereinbelow referred to as alkyl-functional organosilanes, have a total chloride content of below 1000 weight ppm. Usually, total chloride is already below 800 weight ppm.

Yet there are various uses for such alkyltrialkoxysilanes or else alkylalkoxysiloxanes where even these low levels of hydrolyzable chlorides have a disruptive effect. Particularly since, on admission of moisture, the remaining Si—Cl bonds will also hydrolyze and release HCl. The HCl will in turn catalyse the hydrolyzis and condensation reactions of alkyltrialkoxysilanes and alkylalkoxysiloxanes, and can lead to undesired premature reaction and crosslinking. Unintended hydrolyzis in the course of storage can lead to a distinct lowering in the flashpoint of the silane or siloxane.

The engineering required to remove the hydrolyzable chlorides by complete esterification, distillative separation, subsequent neutralization and filtration is costly and inconvenient and reduces plant output. It would desirable to have a simple and quick process for the product streams obtained, more particularly a continuous dechlorination process.

From the start the present invention therefore has for its object to provide a process for dechlorinating alkyl-functional organosilanes, such as alkyltrialkoxysilanes and/or alkylalkoxysiloxanes, which is particularly economical, ideally integral in a continuous operation and preferably requires no liquid or gaseous ammonia or use of strong dissolved bases such as alkali metal alkoxides. A further object is that the alkyl-functional organosilanes, i.e. the alkyl-functional alkoxysilanes or the alkyl-functional alkoxysiloxanes, are not condensed and also ideally especially the alkoxy groups in the organosilanes are not hydrolyzed.

These objects are achieved by the novel process and use corresponding to the features of Claims 1 to 15; advantageous embodiments are set forth in dependent claims and in detail in the description.

It was found that, surprisingly, the chloride atoms of the Si—Cl bonds in the alkyl-functional organosilanes can be exchanged for hydroxide ions using suitable ion exchanger resins to form Si—OH. This process will prove to be a simple and rapid process in which the treatment of product streams with an anion exchanger makes it possible to exchange the chloride ions for hydroxide ions on the silicon atoms of alkyl-functional organosilanes. Proceeding according to the process of the invention, the chlorine atoms in Si—Cl bonds become hydrolyzed and/or existing HCl is neutralized and more particularly becomes bound to the anion exchanger. A particular advantage of the process according to the invention is that the anion exchange resins can be regenerated if necessary, and so further cost-savings are possible. The anion exchanger resins used can preferably be repeatedly regenerated and reused in the process.

It was further found that, surprisingly, not only alkyltrialkoxysilanes, such as isobutyltriethoxysilane, but also the oligomeric products such as, for example, alkylalkoxysiloxanes, interchangeably oligo(alkylalkoxysiloxane), especially oligo(propylethoxysiloxane), can be treated with the same ion exchange resin to achieve a distinct reduction in the level of hydrolyzable chlorides.

It is particularly advantageous that the level of hydrolyzable chloride in weight ppm can be reduced by at least 80% using the process according to the invention, and that the resulting products otherwise remain chemically essentially unchanged in a particularly advantageous manner, and it is particularly advantageous for the alkyl-functional organosilanes, such as the alkyltrialkoxysilanes and/or alkylalkoxysiloxanes, not to oligomerize any further and preferably also remain stable in storage. It is particularly preferable for the level of hydrolyzable chloride in the alkyl-functional organosilanes having a chlorine content to be reducible by at least 80%, especially by at least 85%, preferably by at least 90%, more preferably by at least 92%, even more preferably by at least 95% and yet even more preferably by at least 98% by the contacting with a weak basic anion exchanger.

The invention provides a process for preparing alkyl-functional organosilanes essentially free of chlorine, by contacting alkyl-functional organosilanes having a chlorine content with a weald basic anion exchanger to obtain alkyl-functional organosilanes essentially free of chlorine, and preferably the process can be carried out in a continuous manner. Batch operation of the process can likewise be preferable if it is integrated in a batch process for production of alkyl-functional organosilanes.

Chlorine-functional organosilanes or organosilanes having a chlorine content are the organosilanes complying with the definition according to the invention, where chlorine-functional is to be understood as meaning exclusively Si—Cl bonds. An organosilane having a chlorine content may in accordance with the present invention have hydrolyzable Si—Cl moieties/Si—Cl bonds and/or free HCl.

Alkyl-functional organosilanes essentially free of chlorine are understood by this invention to be alkyl-functional organosilanes which have been contacted with a basic anion exchanger and whose content of chlorides selected from chlorine in HCl or Si—Cl bonds is reduced compared with the starting compounds, i.e. alkyl-functional organosilanes having a chlorine content; more particularly the weight ppm chloride content is reduced by at least 50%, especially by 60% and more preferably by at least 70% and, according to the invention, by at least 80%. Preferably, their chlorine content is reduced by at least 85%, preferably by at least 90%, more preferably by at least 92%, even more preferably by at least 95% and yet even more preferably by at least 98% relative to the untreated organosilanes. The essentially chlorine-free alkyl-functional organosilanes comprise alkyl- and hydroxy-functional organosilanes or alkyl-, hydroxy- and alkoxy-functional organosilanes, such as preferably hydroxyl-containing alkylalkoxysilanes and/or hydroxyl-containing oligo(alkylalkoxysiloxane)s, which more particularly have essentially no longer any Si—Cl moiety and/or free HCl.

According to the invention, the weight ppm chloride/chlorine content of the alkyl-functional organosilanes essentially free of chlorine is at least 80% reduced relative to the weight ppm chlorine content of the alkyl-functional organosilanes used in the process. It is further preferable for the weight ppm chloride content of alkyl-functional organosilanes essentially free of chlorine to be reduced by at least 85%, preferably by at least 90%, more preferably by at least 92%, even more preferably by at least 95% and yet even more preferably by 98% relative to the weight ppm chlorine content of alkyl-functional organosilanes used in the process. Depending on the alkyl-functional organosilane and the starting concentration of chloride, the flow rate and the contact time with the anion exchanger, the chlorine content can preferably be reduced to below 100 weight ppm and preferably to below 50 weight ppm in the alkyl-functional organosilanes.

According to the invention, the alkyl-functional organosilanes essentially free of chlorine comprise organosilanes of the general formula I or alkyl-functional silanes and/or alkyl-functional siloxanes derived therefrom by hydrolyzis or by hydrolyzis and condensation respectively,

where
R¹ in each case independently represents a linear, branched or cyclic alkyl radical having 2 to 18 carbon atoms, and R² in each occurrence independently represents a hydrogen, a linear, branched and/or cyclic alkyl radical having 1 to 4 carbon atoms, and R³ represents a linear, branched or cyclic alkyl radical having 1 to 8 carbon atoms, and x is =0 or 1, preferably x=0.

In this connection, alkyl-functional organosilanes having a chlorine content shall be taken to be, for the purposes of the invention, alkyl- and chlorine-functional organosilanes, especially chlorine-functional alkylalkoxysilanes and/or chlorine-functional oligo(alkylalkoxysiloxane)s. It is particularly preferable for the alkyl-functional organosilanes having a chlorine content to comprise organosilanes of the general formula II or alkyl-functional silanes, such as alkylalkoxysiloxanes with silanol groups, and/or alkyl-functional siloxanes derived therefrom by hydrolyzis or by hydrolyzis and condensation respectively,

where R¹ in each case independently represents a linear, branched or cyclic alkyl radical having 2 to 18 carbon atoms, and R² in each occurrence independently represents a hydrogen, a linear, branched and/or cyclic alkyl radical having 1 to 4 carbon atoms, and R³ represents a linear, branched or cyclic alkyl radical having 1 to 8 carbon atoms, and Cl is hydrolyzable chlorine, wherein y is =1, 2 or 3 and x is =0 or 1, with the proviso that x+y in formula II is =3 and preferably x=0. Replacing the chlorides in compounds of formula II, or in the siloxanes derived therefrom, by OH groups on an anion exchanger gives the chlorine-free alkyl-functional organosilanes, especially of formula I or the corresponding siloxanes. It is a particular advantage of the process according to the present invention that the alkyl-functional organosilanes having a chlorine content preferably are essentially not condensed by the weak basic anion exchangers; more particularly, the alkylalkoxysilanes and/or the oligo(alkylalkoxysiloxane)s do not condense in the presence of the anion exchangers.

In one alternative, the alkyl-functional organosilanes having a chlorine content also or additionally to the hydrolyzable chlorine in Si—Cl bonds include free chlorides, for example in the form of HCl. Free chlorides may form/have formed by hydrolyzis from alkyl-functional organosilanes having hydrolyzable chlorides, or else correspond to a hydrolyzis and/or condensation catalyst which is to be removed in order that any further hydrolyzis and/or condensation reaction of oligo(alkylalkoxysiloxane)s may be avoided. The HCl catalyst may come for example from the conversion of alkylalkoxysilanes into oligo(alkylalkoxysilane)s or from the esterification of alkylchlorosilanes with alcohols.

In alkyl-functional organosilanes containing chlorine, that is hydrolyzable chlorine, especially chlorine-functional alkylalkoxysilanes and/or alkylalkoxysilanes containing HCl, the hydrolyzable chloride content is reducible by at least 80%, especially by at least 85%, preferably by at least 90%, more preferably by at least 92%, even more preferably by at least 95% and yet even more preferably by at least 98%, preferably at flow rates of 0.01 m/h to 15 m/h and preferably up to 5 m/h, while more particularly the alkylalkoxysilanes are not condensed and while preferably the anion exchanger column is 3 cm in diameter and 15 cm in height. Very good results for reducing hydrolyzable chlorine by up to 80% are also achieved at flow rates of up to 10 m/h.

In alkyl-functional oligo(alkylalkoxysiloxane) containing chlorine, that is hydrolyzable chlorine, especially chlorine-functional oligo(alkylalkoxysiloxane)s and/or oligo(alkylalkoxysiloxane)s containing HCl, the hydrolyzable chloride content is reducible by at least 80%, especially by at least 85%, preferably by at least 90%, more preferably by at least 92%, even more preferably by at least 95% and yet even more preferably by at least 97%, preferably at flow rates of 0.01 m/h to 15 m/h and preferably up to 3.3 m/h, more preferably up to 0.5 m/h, while more particularly the oligo(alkylalkoxysilane)s are not condensed further and while preferably the anion exchanger column is 3 cm in diameter and 15 cm in height. Very good results for reducing hydrolyzable chlorine by up to 97% are also achieved at flow rates of up to 0.1 m/h and preferably up to 0.5 m/h.

According to the present invention, the weak basic anion exchanger contains nitrogen-containing groups; more particularly, the weak basic anion exchanger having nitrogen-containing groups is in the solid phase. It is further preferable for the weak basic anion exchanger to comprise quaternary hydrocarbon-substituted ammonium groups and/or tertiary hydrocarbon-substituted amine groups; more particularly, the anion exchanger is in the solid phase and preferably bonded covalently to the carrier of the anion exchanger. Preferably, the anion exchanger is used in the solid phase and in the OH form or as free base.

Therefore, suitable anion exchangers that are not in the OH form are converted into the OH form before use in the process of the present invention, preferably by means of an aqueous or aqueous-alcoholic alkali metal hydroxide solution. Optionally, the weak basic anion exchanger also comprises secondary hydrocarbon-substituted amine groups or primary ones, in which case the anion exchangers mentioned preferably constitute polystyrene or styrene-divinylbenzene copolymers.

It is likewise preferable for the alkyl-functional organosilanes having a chlorine content to be contacted with the anion exchanger in the presence of an alcohol, especially in the presence of ethanol and/or methanol and particularly preferably with ethanol when the alkoxy groups in the organosilane are ethoxy groups, or with methanol in the case of methoxy groups.

It is particularly preferable for the anion exchanger to have a carrier, especially a carrier polymer, preferably a polystyrene, with nitrogen-containing groups, especially with quaternary hydrocarbon-substituted ammonium groups and/or with tertiary hydrocarbon-substituted amine groups. The carrier is preferably in the form of porous particles and these particles more preferably have a diameter in the range from 0.01 to 2 mm, and especially in the range from 0.3 to 1.25 mm, and preferably 90% of the particles have a diameter in the range from 0.315 to 1.25 mm. It is further preferable for the particles to be macroporous.

A suitable basic anion exchanger for the process of the present invention has a pH in water of below <10 at a concentration of 10% by weight in water, and it shall be taken to be a weak basic anion exchanger when it preferably has under the conditions mentioned a pH below <9 and more preferably below <8. An anion exchanger shall likewise be taken to be suitable when it essentially catalyses the hydrolyzis and condensation during the contacting only minimally, if at all. The hydrolyzis and/or condensation can also be reduced owing to steric hindrance or owing to precise process management, time, flow rate, and is/can then be less dependent on the pH.

In the process of the present invention, the anion exchanger has a carrier polymer with quaternary alkylammonium groups and/or with tertiary dialkylamino groups, wherein especially the quaternary alkylammonium groups have essentially hydroxide ions as counter-ions and/or the tertiary dialkylamino groups are in the form of the free base. It is particularly preferable in this connection for the basic anion exchanger to be a styrene-divinylbenzene copolymer with trialkylammonium groups, especially in the OH form, and/or a styrene-divinylbenzene copolymer with dialkylamino groups in free base form. When basic anion exchangers comprising a styrene-divinylbenzene copolymer with trialkylammonium groups in the chloride form are used, the chlorides are converted into the OH form before use, for example with an alkali metal hydroxide solution. Alkali metal hydroxide solutions used are preferably aqueous solutions of potassium hydroxide, sodium hydroxide or else other water- or water-alcohol-soluble bases such as ammonia or alkali metal carbonates such as $Na_2CO_3$. After conversion of the anion exchanger into the OH form and before contacting with the alkyl-functional organosilanes, the anion exchanger is flushed with an alcohol in order to displace excess water in particular. The alcohol used is preferably the alcohol which would be formed by hydrolyzis of the respective alkoxy groups: methanol in the case of methoxy groups in the organosilane or ethanol in the case of ethoxy groups in the organosilane.

Quaternary ammonium groups shall be deemed to include not only alkylammonium groups but also N-alkylimine-functional groups, such as N-alkylpyridinium groups. Suitable alkyl groups contain 1-20 carbon atoms, preferably from 1 to 4 carbon atoms, and are preferably methyl or ethyl groups. According to the present invention, the weak basic anion exchangers are loaded with hydroxide ions and more particularly they have nitrogen-containing groups.

The process can be carried out with particular preference by using as anion exchangers purely organic amino-functional resins, especially amino-functionalized, aromatic polymers having alkyl-functionalized secondary, tertiary and/or quaternary amino groups, in which case tertiary and quaternary groups are preferable. The alkyl groups may be linear, branched or cyclic and preferably they are methyl or ethyl. Amino-functionalized divinylbenzene-styrene copolymers can be used according to the present invention, i.e. divinylbenzene-crosslinked polystyrene resin, in which case those from the group of dialkylaminomethylene-functionalized divinylbenzene-styrene copolymers or trialkylaminomethylene-functionalized divinylbenzene-styrene copolymers are particularly preferable, especially with alkyl being methyl or ethyl, preference being given to dimethyl- or trimethylaminomethylene-functionalized divinylbenzene-styrene copolymers.

In addition to the dimethylamino-functionalized divinylbenzene-crosslinked, porous polystyrene resins, the process of the present invention or the use according to the present invention can also utilize further divinylbenzene-crosslinked, porous polystyrene resins functionalized with quaternary and also optionally tertiary amino groups. The resins or the basic anion exchangers used according to the invention are all notable for a high specific surface area, porosity and high chemical stability.

What will prove particularly suitable for the process according to the invention or the use is divinylbenzene-crosslinked polystyrene resin with quaternary ammonium groups, according to the invention a styrene-divinylbenzene copolymer with trialkylammonium groups in the chloride form, such as Lewatit K 6362, wherein the chlorides were exchanged for hydroxides, so that a styrene-divinylbenzene copolymer with trialkylammonium groups in the OH form is used according to the invention. It is obtainable in spherical beads having an average diameter of about 0.62+/−0.05 mm. Bulk density is about 690 kg/m$^3$.

What is likewise particularly suitable for the process according to the invention or the use is a divinylbenzene-crosslinked polystyrene resin with dimethylamino groups in the form of the free base, such as Lewatit MP 62, having a particle diameter of 0.315 to 1.25 mm for 90% of the particles.

What will likewise prove suitable for the process according to the invention or the use is divinylbenzene-crosslinked polystyrene resin with tertiary amino groups, such as Amberlyst A21 ion exchanger resin based on divinylbenzene-crosslinked polystyrene resin with dimethylaminomethylene groups on the polymeric backbone of the resin. Amberlyst® A21 is a weak basic anion exchanger resin which is obtainable in the form of the free base and in spherical beads having an average diameter of about 0.49 to 0.69 mm and a water content of up to 56% to 62% by weight relative to the overall weight. Surface area is about 25 m²/g and average pore diameter is 110 angström.

The process according to the invention and the use according to the invention can likewise employ Amberlyst A 26 OH, which is based on a quaternary trimethylamino-functionalized divinylbenzene-styrene copolymer and has a highly porous structure. The average particle diameter of the resin is typically in the range from 0.56 to 0.70 mm. The resin is marketed as ionic form. The water content can be 66% to 75% by weight relative to the overall weight. Surface area is about 30 m²/g for an average pore diameter of 400 angström.

It is particularly preferable for an anion exchanger of a styrene-divinylbenzene copolymer with trialkylammonium groups which is in the Cl form to be converted into the OH form with an aqueous alkali metal hydroxide solution, and be used as a weak basic anion exchanger. This process step is applicable in the start-up of the process when the anion exchanger can be commercially obtained in the Cl form, but also as a recycling step to regenerate a spent anion exchanger.

According to the present invention, the alkyl-functional organosilanes having a chlorine content comprise monomeric alkylalkoxysilanes and/or oligomeric alkylalkoxysiloxanes such as oligo(alkylalkoxysiloxane), which each have a content of the respective incompletely esterified silanes and/or siloxanes and more particularly have the unconverted Si—Cl moieties and/or free chlorides, for example as HCl, especially but not conclusively propyltrialkoxysilane, butyltrialkoxysilane, hexyltrialkoxysilane, cyclohexyltrialkoxysilane, octyltrialkoxysilane, preferably butyltriethoxysilane, butyltrimethoxysilane, n-butyltriethoxysilane, n-butyltrimethoxysilane, isobutyltriethoxysilane, isobutyltrimethoxysilane, n-propyltriethoxysilane, isopropyltriethoxysilane, n-propyltrimethoxysilane, isopropyltrimethoxysilane, hexyltriethoxysilane, hexyltrimethoxysilane, isohexyltriethoxysilane, isohexyltrimethoxysilane, n-hexyltriethoxysilane, n-hexyltrimethoxysilane, cyclohexyltriethoxysilane, cyclohexyltrimethoxysilane, octyltriethoxysilane, octyltrimethoxysilane, n-octyltriethoxysilane, n-octyltrimethoxysilane, isooctyltriethoxysilane, isooctyltrimethoxysilane, and/or oligomeric alkylalkoxysiloxanes such as oligo(alkylalkoxysiloxane)s comprising, preferably, oligo(alkylalkoxysiloxane) i.e. oligomeric alkylalkoxysiloxanes, such as especially oligo(propylalkoxysiloxane), oligo(propylethoxysiloxane), oligo(propylmethoxysiloxane), oligo(butylalkoxysiloxane), oligo(butylethoxysiloxane), oligo(butylmethoxysiloxane), oligo(hexylalkoxysiloxane), oligo(hexylethoxysiloxane), oligo(hexylmethoxysiloxane), oligo(octylalkoxysiloxane), oligo(octylethoxysiloxane), oligo(octylmethoxysiloxane), which partly have a content of the respective incompletely esterified silanes and/or siloxanes, i.e. which have unconverted Si—Cl moieties and/or else already hydrolyzed chlorides from Si—Cl moieties, for example as HCl, and/or HCl as hydrolyzis and/or condensation catalyst. It is further preferable in this connection for the oligo(alkylalkoxysiloxane)s to have a degree of oligomerization of between 2 to 30 Si atoms per oligomer.

For the purposes of the present invention, alkyl-functional organosilanes having a content of chlorine or chlorine content further include oligomeric alkylalkoxysiloxanes such as oligo(alkylalkoxysiloxane) which preferably have a molar mass in the range from 200 to 3000 g/mol. Molar mass can be measured using the GPC method familiar to a person skilled in the art.

Molar mass measured via GPC is preferably in the range of 200-3000, and it is more preferable for the average molar mass to be in the range from 500 to 1300, more preferably between 500-1000 and more preferably between 600-800 g/mol. A person skilled in the art will appreciate that when molar masses are too high, the viscosity can be too high and a satisfactory flow rate is only achievable by diluting with a solvent.

Exchanging the chlorine atoms of the Si—Cl moieties for Si—OH and/or removing the free chlorides converts the aforementioned alkyl-functional organosilanes having a chlorine content, or a content of chlorine, into the products according to the present invention, the essentially chlorine-free alkyl-functional organosilanes, especially of formula I and/or the siloxanes derived by hydrolyzis and/or condensation.

The invention likewise provides a process in which the alkyl-functional organosilanes having a chlorine content are contacted with the anion exchanger at a flow rate of 0.01 m/h up to 15 m/h to obtain more particularly alkyl-functional organosilanes essentially free of chlorine, while the flow rate is preferably between 0.1 m/h to 11 m/h, more preferably around 0.2 to 11 m/h, even more preferably between 0.4 to 10.5 m/h (meter/hour), or alternatively up to 3.3 m/h, 5 m/h or even up to 10 m/h.

It is likewise preferable for the alkyl-functional organosilanes having a chlorine content to be contacted with the anion exchanger in an ion exchanger column at a flow rate of 0.01 m/h up to 15 m/h to obtain alkyl-functional organosilanes essentially free of chlorine, while the ion exchanger column has an internal diameter of 3 cm and especially a height of 15 cm. A person skilled in the art will appreciate that the dimensioning of the ion exchanger column can be varied as a function of the flow rate, the viscosity of alkyl-functional organosilanes, the particle size of the carrier of the ion exchangers and the desired amount of product stream.

It is a further part of the subject matter of the process according to the present invention that the alkyl-functional organosilanes which have been contacted with an anion exchanger may subsequently be further reduced in the chloride content by treatment with a metal alkoxide, especially in a distillative working-up step. The product thus obtained preferably contains less than 25 weight ppm of chloride.

The invention further provides for the use of a weak basic anion exchanger to exchange the chlorine atoms in chlorosilane bonds of alkyl-functional organosilanes for hydroxyl groups or to remove hydrolyzis and/or condensation catalysts in the form of acids and/or to remove HCl. The HCl can result from hydrolyzed Si—Cl moieties or else correspond to the hydrolyzis and/or condensation catalyst. The anion exchangers defined above are used as weak basic anion exchangers. Removal of hydrolyzis and/or condensation catalyst is preferable to avoid any further hydrolyzis and/or condensation reaction of oligo(alkylalkoxysiloxane)s, for example in order to enhance the storage stability of oligo(alkoxysiloxane)s.

The examples which follow describe the process of the invention more particularly without limiting the invention to these examples.

EXAMPLES

Lewatit K 6362 ion exchanger (styrene-divinylbenzene copolymer with trialkylammonium groups) is stored in the Cl⁻ form. The resin was converted into the OH⁻ form (styrene-divinylbenzene copolymer with trialkylammonium groups and OH⁻ ions) by flushing with 5% aqueous KOH. Lewatit MP 62 ion exchanger resin (styrene-divinylbenzene copolymer with dimethylamino groups in the form of the free base) is stored in the OH⁻ form. The ion exchanger column used had a diameter of 3 cm and a height of 15 cm. Before applying the alkyltrialkoxysilanes/alkylalkoxysiloxanes, the ion exchanger resins were each flushed with ethanol (EtOH) to displace excess water. Potentiometric determination of hydrolyzable chloride: the level of hydrolyzable chloride in the alkyl-functional organosilanes in weight ppm is titrated potentiographically with silver nitrate. The w % in the examples correspond to % by weight.

Example 1

100 g of isobutyltriethoxysilane (IBTEO, hydrolyzable chloride content: 156 ppm) were passed at a flow rate of 5 m/h over Lewatit K 6362 ion exchanger (available from Lanxess) in the OH⁻ form. After working up, 87.7 g of IBTEO with <2 ppm of hydrolyzable chloride were obtained. The ethanol content of the product obtained after eluation was 5 w % EtOH. EtOH was removed in a rotary evaporator. The resulting IBTEO had a distinct amine odour. The basic ion exchanger used had a pH of 8.7.

Example 2

866 g of isobutyltriethoxysilane (IBTEO, hydrolyzable chloride content: 942 ppm) were passed at a flow rate of 5 m/h over Lewatit MP 62 ion exchanger (available from Lanxess) in the OH⁻ form. After working up, 862 g of IBTEO with 84 ppm of hydrolyzable chloride were obtained. The ethanol content of the product obtained after eluation was 4 w % EtOH. EtOH was removed in a rotary evaporator. The isolated IBTEO was odourless. The basic ion exchanger used had a pH of 7.2.

Example 3

176 g of isobutyltriethoxysilane (IBTEO, hydrolyzable chloride content: 3600 ppm) were passed at a flow rate of 10 m/h over Lewatit MP 62 ion exchanger (available from Lanxess) in the OH⁻ form. After working up, 153 g of IBTEO with 577 ppm of hydrolyzable chloride were obtained. The ethanol content of the product obtained after eluation was 13 w % EtOH. EtOH was removed in a rotary evaporator. The isolated IBTEO was odourless.

Example 4

212 g of oligo(propylalkoxysilane) (hydrolyzable chloride content: 4100 ppm) were passed at a flow rate of 0.5 m/h over Lewatit MP 62 ion exchanger (available from Lanxess) in the OH⁻ form. After working up, 176 g of oligo(propylalkoxysilane) having 104 ppm of hydrolyzable chloride were obtained. The ethanol content of the odourless product obtained after eluation was 17 w % EtOH. EtOH was removed in a rotary evaporator.

Example 5

208 g of oligo(propylalkoxysilane) (hydrolyzable chloride content: 3800 ppm) were passed at a flow rate of 3.3 m/h over Lewatit MP 62 ion exchanger (available from Lanxess) in the OH⁻ form. After working up, 181 g of oligo(propylalkoxysilane) having 1043 ppm of hydrolyzable chloride were obtained. The ethanol content of the odourless product obtained after eluation was 13 w % EtOH. EtOH was removed in a rotary evaporator.

Example 6

The products of Examples 1 to 6 and also alkylsiloxane treated with 3% alkali metal alkoxide were analysed by GC/GPC several weeks after treatment. In each case, the change in purity and/or molar mass after storage of products treated with basic ion exchangers was minimal. By contrast, the siloxane treated with alkali metal alkoxide is observed to have undergone a significant increase in molar mass.

| Example | Product | Purity[1] | Purity[2] | Molar mass $M_W$ (g/mol)[1] | Molar mass $M_W$ (g/mol)[2] |
|---|---|---|---|---|---|
| 1 | IBTEO | 99.1% | n.d. | | |
| 2 | IBTEO | 98.8% | 98.3%[2] | | |
| 3 | IBTEO | 98.8% | 97.0%[3] | | |
| 4 | siloxane | | | 737 | 732[5] |
| 5 | siloxane | | | 737 | 754[6] |
| 6 | siloxane(3) | | | 737 | 1042 |

[1]before treatment
[2]after treatment and storage
[3]siloxane was treated with 3% alkali metal alkoxide
n.d. not determined

Example 7

Alkylsiloxanes having a high chloride content of 223 weight ppm and a low chloride content of 42 weight ppm were stored under identical conditions. The flashpoints of the alkylsiloxanes were checked to DIN EN ISO 2719 during the several months of storage. The changes in flashpoints are diagrammed in FIG. 1.

The invention claimed is:

1. A process for preparing an alkyl-functional organosilane essentially free of chlorine, comprising contacting an alkyl-functional organosilane having a chlorine content with a basic anion exchanger to prepare the alkyl-functional organosilane essentially free of chlorine, wherein the alkyl-functional organosilane essentially free of chlorine is a siloxane derived from an alkyl-functional organosilane of formula I by hydrolysis and condensation:

$$R^1—Si(R^3)_x(OR^2)_{3-x} \qquad (I)$$

wherein
R¹ in each case independently is a linear, branched or cyclic alkyl radical having 2 to 18 carbon atoms,
R² in each occurrence independently is hydrogen, or a linear, branched or cyclic alkyl radical having 1 to 4 carbon atoms,
R³ is a linear, branched or cyclic alkyl radical having 1 to 8 carbon atoms, and
x is =0 or 1,
or
the alkyl-functional organosilane having a chlorine content is a siloxane derived from an alkyl-functional organosilane of formula II by hydrolysis and condensation:

$$R^1—Si(R^3)_xCl_y(OR^2)_{3-x-y} \qquad (II)$$

wherein
R¹ in each case independently is a linear, branched or cyclic alkyl radical having 2 to 18 carbon atoms,
R² in each occurrence independently is hydrogen, or a linear, branched or cyclic alkyl radical having 1 to 4 carbon atoms,
R³ is a linear, branched or cyclic alkyl radical having 1 to 8 carbon atoms,
Cl is hydrolyzable chlorine,
y=1, 2 or 3, and
x=0 or 1,
with the proviso that x+y in formula II is 1, 2, or 3.

2. The process according to claim 1, wherein the basic anion exchanger comprises a group comprising nitrogen.

3. The process according to claim 1, wherein the basic anion exchanger has a carrier with a quaternary hydrocarbon-substituted ammonium group, a tertiary hydrocarbon-substituted amine group, or both.

4. The process according to claim 1, wherein the basic anion exchanger has a carrier polymer with a quaternary alkylammonium group, a tertiary dialkylamino group, or both.

5. The process according to claim 1, wherein the basic anion exchanger is a styrene-divinylbenzene copolymer with a trialkylammonium group in a $OH^-$ form, a styrene-divinylbenzene copolymer with a dialkylamino group in free base form, or both.

6. The process according to claim 5, further comprising converting an anion exchanger of a styrene-divinylbenzene copolymer with a trialkylammonium group in a Cl form into the $OH^-$ form with an aqueous alkali metal hydroxide solution, wherein the basic anion exchanger is a weak basic anion exchanger.

7. The process according to claim 1, wherein the alkyl-functional organosilane essentially free of chlorine is the siloxane derived from the alkyl-functional organosilane of formula I.

8. The process according to claim 1, wherein the alkyl-functional organosilane having a chlorine content is the siloxane derived from the alkyl-functional organosilane of formula II.

9. The process according to claim 1, wherein the siloxane having a chlorine content comprises an oligomeric alkylalkoxysiloxane, having a content incompletely esterified siloxane.

10. The process according to claim 1, wherein a weight ppm chloride content of the siloxane essentially free of chlorine is at least 80% reduced relative to a weight ppm chloride content of the siloxane in the process.

11. The process according to claim 1, wherein the siloxane having a chlorine content is contacted with the basic anion exchanger at a flow rate of from 0.01 m/h to 15 m/h.

12. The process according to claim 1, wherein the siloxane having a chlorine content is contacted with the basic anion exchanger in the presence of an alcohol.

13. The process according to claim 1, wherein the basic anion exchanger is a weak basic anion exchanger suitable for at least one selected from the group consisting of substituting Si—OH for Si—Cl in alkyl-functional chloride-comprising siloxane, removing hydrolysis, condensation catalysts in the form of acids and removing hydrogen chloride.

14. The process according to claim 1, wherein the siloxane essentially free of chlorine has a stable flashpoint for a storage period of several months.

15. The process according to claim 8, wherein, in formula II, x=0.

* * * * *